United States Patent [19]
Andersson

[11] Patent Number: 5,312,592
[45] Date of Patent: May 17, 1994

[54] DISPOSABLE KIT FOR PREPARATION

[75] Inventor: Henry Andersson, Upsala, Sweden

[73] Assignee: Scanditronix AB, Upsala, Sweden

[21] Appl. No.: 945,257

[22] Filed: Sep. 15, 1992

[51] Int. Cl.$^5$ ............................................. G01N 35/00
[52] U.S. Cl. ..................................... 422/61; 422/102; 422/68.1; 422/104
[58] Field of Search .................... 422/100, 102, 63, 61, 422/103, 104, 68.1; 206/569, 570; 424/1.1, 9

[56] References Cited

U.S. PATENT DOCUMENTS

| | | | |
|---|---|---|---|
| 3,774,035 | 11/1973 | Litt ........................................ | 424/1.1 |
| 3,791,982 | 2/1974 | Lewis et al. ........................... | 424/1.1 |
| 3,950,643 | 4/1976 | Charlton ............................... | 424/1.1 |
| 4,087,248 | 5/1978 | Miles ..................................... | 424/1.1 |
| 4,160,803 | 7/1979 | Potts ..................................... | 206/509 |
| 4,250,161 | 2/1981 | de Schrijver ............................ | 424/1 |
| 4,272,510 | 6/1981 | Smith et al. ............................ | 424/1.1 |
| 4,347,216 | 8/1982 | Kawasaki et al. ..................... | 422/102 |
| 4,565,100 | 1/1986 | Malinoff ............................... | 422/100 |
| 4,675,299 | 6/1987 | Witty et al. ........................... | 206/569 |

FOREIGN PATENT DOCUMENTS

| | | |
|---|---|---|
| 0040186 | 11/1981 | European Pat. Off. . |
| 0165630 | 12/1985 | European Pat. Off. . |
| 2257978 | 11/1981 | Fed. Rep. of Germany . |

Primary Examiner—Robert J. Warden
Assistant Examiner—Hien Tran
Attorney, Agent, or Firm—Young & Thompson

[57] ABSTRACT

An apparatus for the manufacture of radiopharmaceuticals includes a lead chamber (6) and a loading device (5) on which a chemical system is mounted in the form of a disposable kit (5). The apparatus includes a first suspension device (9) which functions to move the loading device in a radiation-safe manner between a loading position externally of the lead chamber and a working position within the lead chamber. A second suspension device is provided for releasing a consumed disposable kit from the loading device, such as to enable the consumed kit to fall down into a bottom section (8) of the lead chamber, this bottom section serving as a waste chamber.

3 Claims, 3 Drawing Sheets

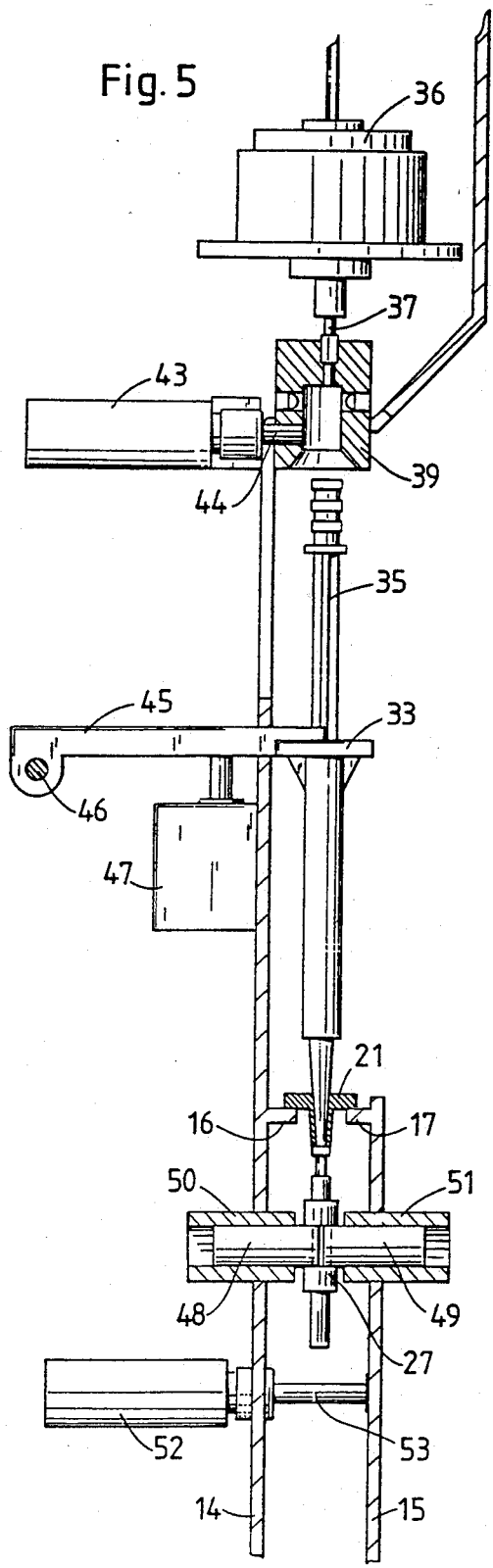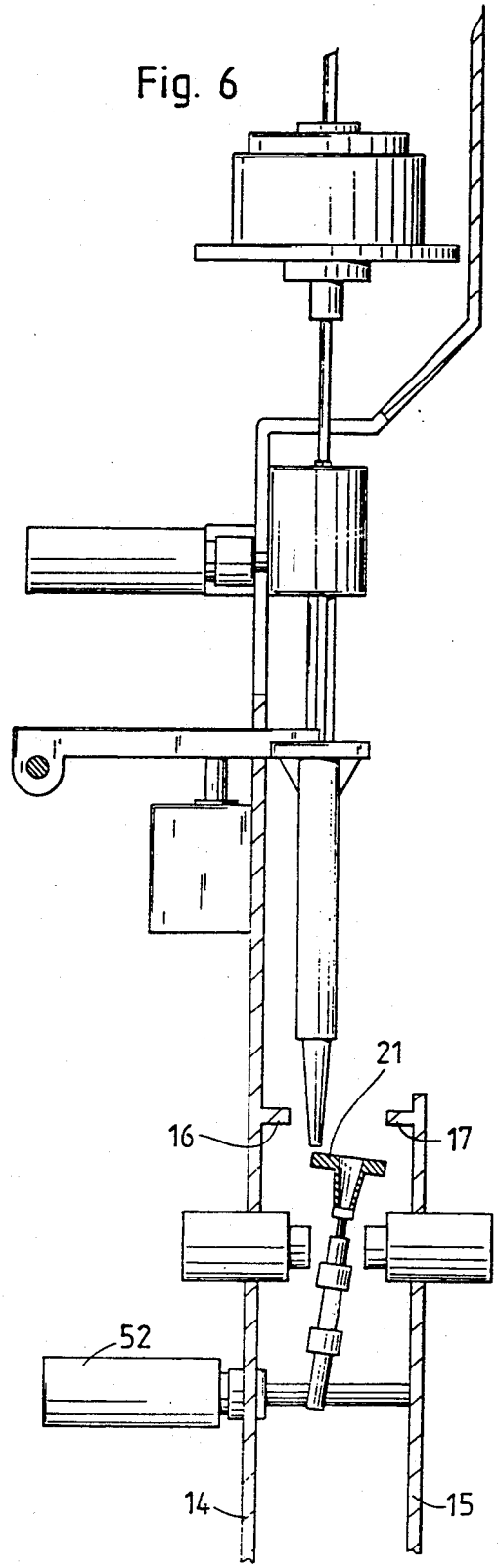

DISPOSABLE KIT FOR PREPARATION

The present invention relates to apparatus for the manufacture of radiopharmaceuticals by chemical reactions based on at least one radiotracer.

More specifically, the apparatus includes a lead chamber which functions as a reaction chamber and also as a radiation shield, a number of containers for accommodating said at least one radiotracers and process liquids, at least one card for supporting a given container, said containers being interconnected by means of hoses and valves and also connected to reaction vessels disposed on the card, said card being intended to be placed in the lead chamber.

An apparatus of this kind is described in our European Patent Specification No. 0 040 186. One drawback with this known apparatus is that the hoses of respective reaction vessels are connected by means of connecting devices to a coupling plate which serves as the lid of the lead chamber. The vessels are mutually connected together by means of coupling hoses which connect the coupling devices one to the other externally of the lead chamber. The use of coupling devices of this kind creates serious sterilization problems. Another drawback with this known apparatus is that it is necessary to leave the cards in their respective card holders until the radioactive radiation in the remaining process liquids has decayed to safe levels. This means that the apparatus cannot be used again until radioactive radiation has ceased, which limits the output performance of the apparatus. The card and the reaction vessels are again brought into use when the radioactive radiation has ceased.

An object of the present invention is to provide an apparatus of the aforedescribed kind which will eliminate the drawbacks of the known apparatus.

Another object of the invention is to provide a disposal card which is intended for one-time use only and which is discarded after use.

Another object of the invention is to provide an apparatus of the aforedescribed kind in which used cards fall down into a waste section located within the lead chamber, whereafter new cards are inserted into the apparatus and a new radiopharmaceutical manufacturing process is initiated with the old cards remaining in the waste container in the lead chamber until radiation has decayed to a safe level.

A further object of the invention is to provide an apparatus of the aforedescribed kind with which the radiation shielding function of the lead chamber is maintained while inserting cards into the apparatus.

BRIEF DESCRIPTION OF THE DRAWINGS

The invention will now be described in more detail with reference to the accompany drawings, in which

FIG. 5 is a cross-sectional view of the units shown in FIG. 4, and illustrates the two moveable walls of the loading device in a first position in which the walls hold the card firmly therebetween; and FIG. 6 is a cross-sectional view similar to the view of FIG. 5 but showing the card holders in mutually separated positions in which they release the card and therewith enable the card to fall down into the waste container in the lead chamber.

FIG. 1 is a perspective view of the inventive apparatus. The apparatus includes three sections 1, 2, 3 which are mounted one above the other and of which the lowermost section 1 forms a waste container for consumed cards, the section 2 functions as a chemical chamber and section 3 is an electronics module. Each section 1-3 comprises a framework of mutually joined aluminium panels or plates. The chemical chamber 2 is provided with an opening 4 in one side panel thereof. A loading device, identified generally at 5, is moveable through the opening 4 between an extended position, in which a card is loaded for insertion into the loading device, as described in more detail herebelow, and an inserted position in which the card is located within the chemical chamber 2. As will be seen from FIGS. 2 and 3, the waste container 1 is provided with radiation shield means in the form of lead plates which surround the side and bottom walls of the waste container or chamber. The chemical chamber 2 is also provided with a lead lining which functions as a radiation shield and surrounds all side walls of the chemical chamber and also its top wall. The lead plates are referenced 6 in the FIGS. 2 and 3 illustrations. Thus, the lead plates 6 delimit an upper section 7 which opens into a lower section 8, the section 7 forming the chemical chamber 2 and the section 8 forming the waste chamber 1.

As shown in FIG. 2, the loading device 5 has a first suspension device 9 in the form of a piston-cylinder device having two ends 10, 11, of which one end, 10, is attached to one side wall of the lead chamber and the other end, 11, is connected to the loading device 5. The piston-cylinder device is preferably a rodless, linear motion device with the piston thereof connected to the loading device 5.

Figure 3:
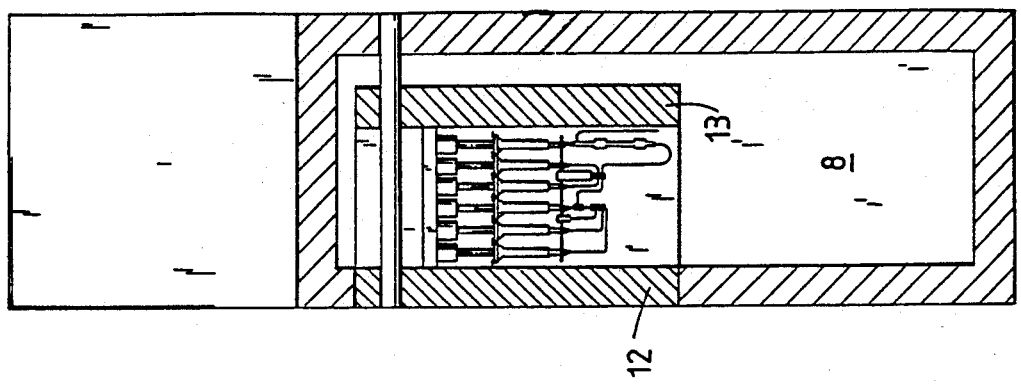
FIG. 3 is a cross-sectional view similar to the view of FIG. 2 but showing the loading device inserted in the apparatus.
Figure 2:
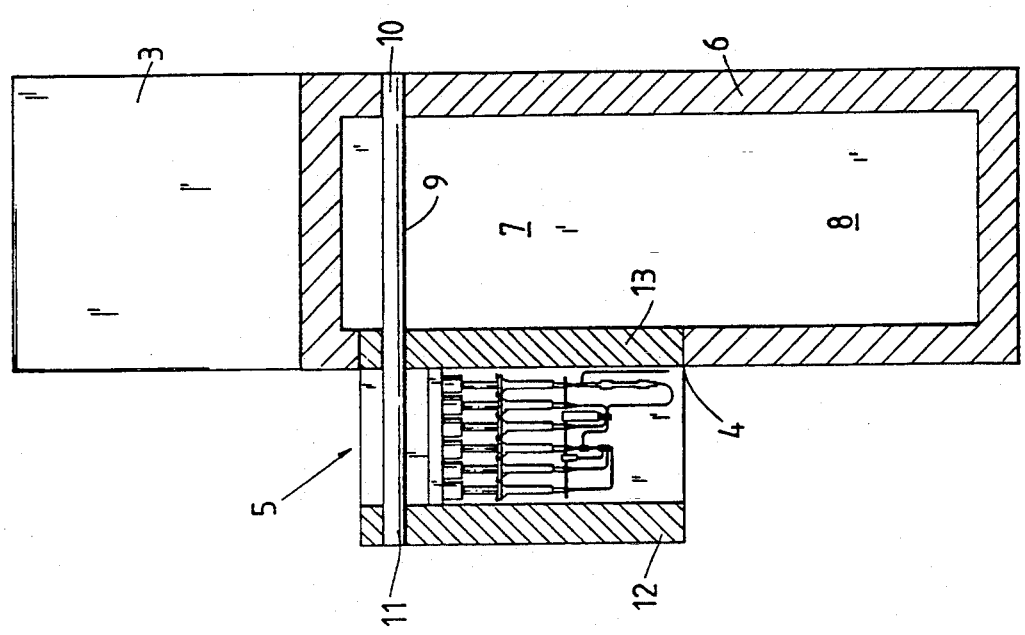
FIG. 2 is a cross-sectional view of the apparatus illustrated in FIG. 1, and shows the loading device extended out from the apparatus.
Figure 1:
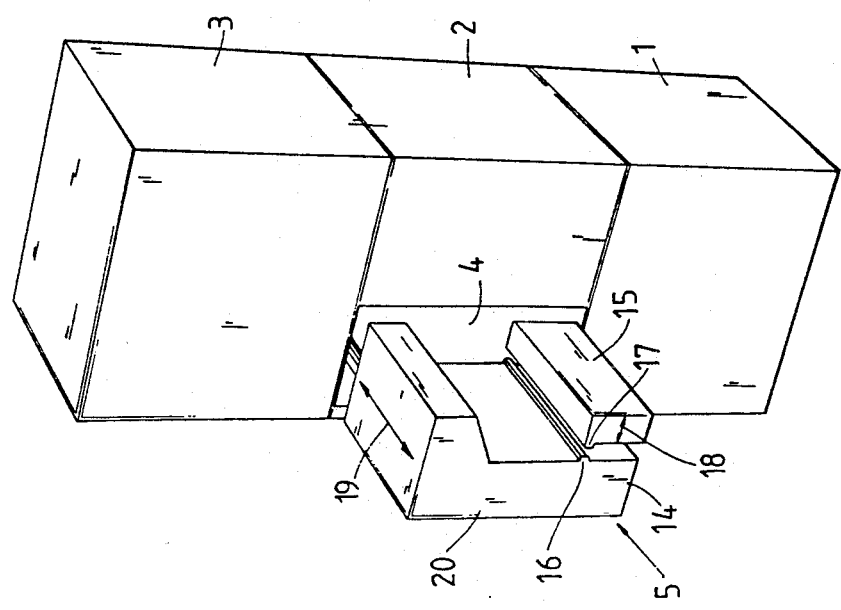
FIG. 1 is a perspective view of the inventive apparatus.

In order to ensure adequate protection against radiation in both the extended and the inserted positions of the suspension device 9, the loading device 5 is provided with a respective first and second lead plate 12, 13, which for the sake of clarity have not been shown in FIG. 1, but which can be seen from FIG. 2. Each lead plate has a contour which corresponds to the contour of the opening 4. When the loading device 5 is extended, as illustrated in FIG. 2, the second lead plate 13 will fully cover the opening 4, so as to prevent radiation emanating from consumed cards lying in the lower section 8 from escaping to the ambient surroundings of the lead chamber. When the loading device 5 is moved into the apparatus, as shown in FIG. 3, the first lead plate 12 prevents radiation that emanates from the radioactive preparations within the lead chamber from escaping to the ambient surroundings.

As illustrated in FIG. 1, the loading device 5 includes a first moveable, vertically arranged wall-section 14 and a second moveable, vertically arranged wall-section 15 which is positioned opposite the first wall-section 14. The first moveable wall-section is provided with a first card holder 16 which is intended to coact with a second card holder 17 mounted on the second wall-section 15. The card holders of the illustrated embodiment have the form of two horizontal strips or bars. The second wall-section 15 can be moved away from and towards the first wall-section 14 with the aid of a second suspension device, not shown in FIG. 1 for the sake of clarity. The directions in which the second wall-section is able to move in relation to the first wall-section are shown by the double-headed arrow 18 in FIG. 1, while the directions in which the first and the second wall-sections 14 and 15 move as a unit are shown by the double-headed arrow 19 in said Figure. This second suspension device will be described in more detail herebelow with reference to FIG. 5.

Figure 4:
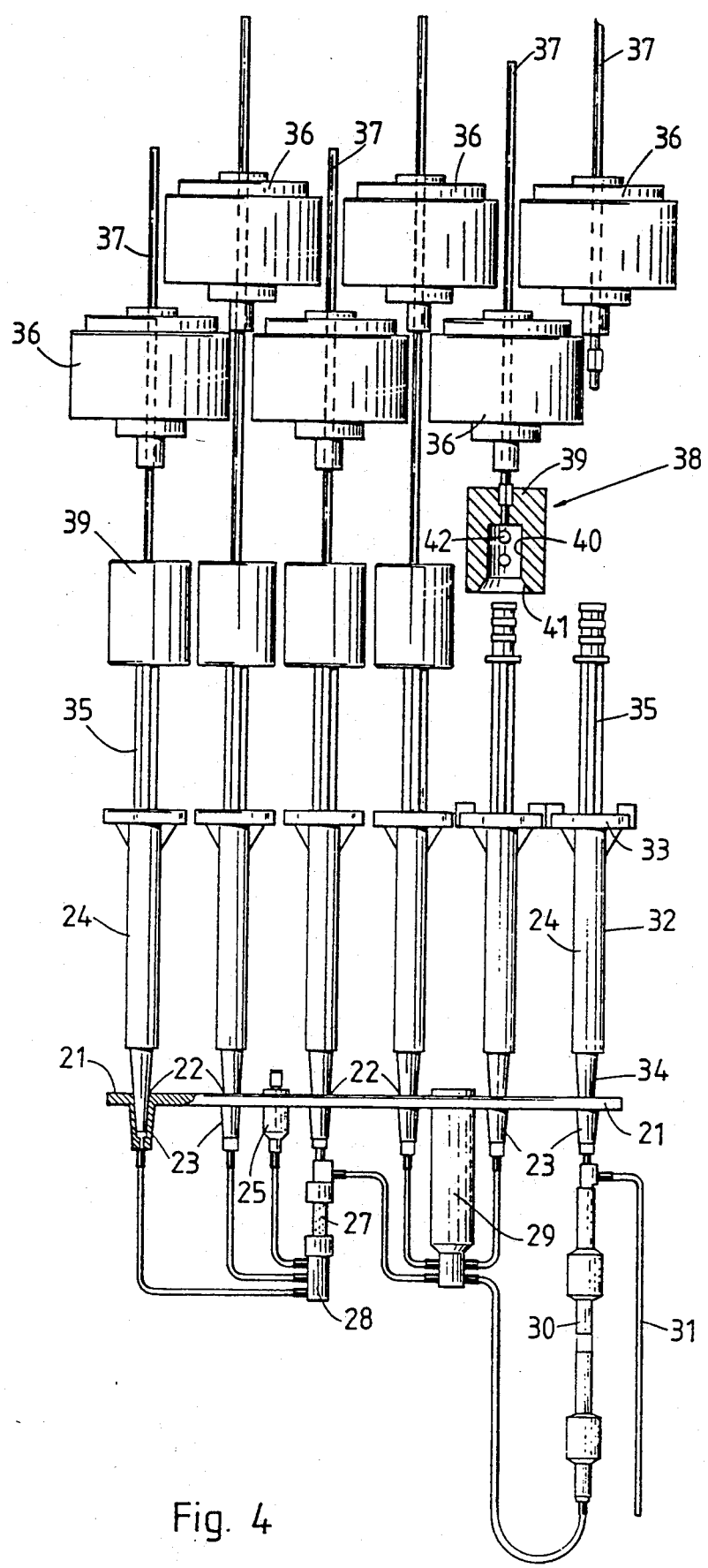
FIG. 4 is a view from above of the card, its hoses and injection devices and shows how the card is mounted in relation to axial stepping motors which function to manoeuvre, the plungers of said injection devices.

The bottom part of FIG. 4 illustrates a card in the form of a disposable kit in accordance with the invention, while the upper part of said Figure illustrates a number of activating devices which are disposed in a widened upper-part 20 of the first wall-section 14. The inventive disposable kit includes a card 21 having the form of an elongated, rigid strip provided with a row of openings as indicated schematically at reference 22. It will also be seen from FIG. 4 that some of the openings 22 are surrounded by sleeves or collars 23 which project out from one main surface of the card and which are formed integrally with said card. These sleeves are intended to support process-liquid injectors 24 on the inner sleeve surfaces. The sleeves are connected to a system of hoses and reaction vessels, as described more clearly herebelow. More specifically, there is included a storage chamber 25 for gas which contains the radiotracer to be treated by the chemical system carried by the card. Provided on the top of the storage chamber 25 is a Luer connection for a gas hose (not shown). A separation column 27 is coupled to the sleeve or collar of the third ejector from the left as seen in the Figure, and arranged beneath this separation column is a branch pipe 28 having connections which lead to the two ejectors located furthest on the left and to the storage chamber 25. A hydrolysis chamber 29 is mounted in an opening 22 on the card and is connected by means of hoses in the manner shown in FIG. 4. Finally, the loading device also includes a de-ionizing chamber 30 which includes a millipore filter, among other things. The radiopharmaceutical produced in the chemical system on the card is removed through a pipe 31. Pinch valves, not shown in the drawings, including a piston-cylinder assembly, function to press a hose against a counterpressure device or anvil means and therewith throttle the flow or process liquid through the hose. Activation of the valves is controlled by the electronics module. The valves are used to guide the process liquids between various units on the card. As will be understood, the components included in the disposable kit will depend on the type of starting material used and the kind of end product desired. Consequently, the various chemical process steps will not be described in detail, since these are not essential to the invention. It is essential to the invention, however, that all reaction vessels, process-liquid containers, gas containers, etc., are arranged on one single disposable card 21. The system of hoses and reaction vessels may be fixedly mounted on a carrier plate (not shown) which, in turn, is connected to the underside of the card 21. This affixation of the said carrier plate and said system may be effected, e.g., by covering the carrier plate and the system of hoses and reaction vessels with a shrink film material. This shrink-film covering will also serve as a sterilization guard.

Each injector 24 includes a cylindrical container 32 having two ends, of which one end carries a flange 33 and the other end carries a tapering cone 34. Each injector also includes a stem 35 having two ends, of which one end is attached to a piston or plunger (not shown) which moves in the cylindrical container 32. Mounted in the widened part 20 of the first moveable wall-section 14 are a number of axial stepping motors 36. The number of stepping motors used will correspond to the number of injectors 32. Each stepping motor has a shaft 37 having two ends. The shaft 37 moves linearly when the stepping motor is activated. A clamping device 38 is mounted on one end of each shaft 37. For the sake of clarity, only one such clamping device 38 is shown in FIG. 4, although it will be understood that each shaft 37 is provided with one such device. The clamping device includes a cylindrical block 39 having a substantially vertical blind-bore 40, the bottom of which presents a funnel-like widening 41 for guiding the other end of a stem 35 into the bore 40. An optical position sensor 42 functions to detect when said end of the stem has reached the bottom of the blind bore 40. When the stem bottoms in the bore 40, a compressed-air pistoncylinder device 43 (shown in FIG. 5) operates to clamp the stem 35 firmly in the bore 40, with the aid of a piston rod 44 which extends through the wall of the cylindrical block and which functions to urge the injector stem against the wall of the cylindrical bore upon activation of the piston-cylinder device 43, said wall of the bore functioning as a counter-pressure surface for clamping the injector stem in the block 39. When the stepping motor 36 is then activated, the shaft of said motor will move the injector stem 35 and therewith also the injector piston (not shown). The piston-cylinder device 43 follows the linear movement of the shaft 37. It will be seen that this arrangement enables process liquids to be metered very accurately and to be transported through the chemical system.

In order to ensure that the injector cone 34 remains firmly seated in the sleeve 23 as the shaft 37 moves upwards, the injector is held pressed into the sleeve with the aid of a lever arm 45 (FIG. 5) having two ends, of which one end is pivotally mounted in the widened part 20 of the first moveable wall 14. The pivot point of the lever arm is referenced 46. The other end of the lever arm is intended for abutment with the injector flange 33 and functions to press the injector downwards. To this end, there is provided a tensioning device in the form of a pressure cylinder 47 which acts on the lever arm 45 in a clockwise direction in FIG. 5. The lever arm 45 also functions to hold the card 21 securely in position, in abutment with the upper side of the strip-like card holders 16, 17.

Also shown in FIG. 5 are two heating jaws 48 and 49, which can be moved towards and away from the separation column 27 for the purpose of heating the process liquid flowing through said column, movement of said jaws being effected with the aid of means (not shown), for example a compressed-air piston-cylinder device similar to the piston-cylinder device 43. Each heating jaw 48, 49 has the form of an aluminium block in which a heat-generating device is mounted, for example an electrical resistance wire. Each heating jaw 48, 49 is moveably mounted in a respective cylindrical housing 50 and 51 which are fixedly mounted on the first moveable wall 14 and the second moveable wall 15 respectively. Each heating jaw has a front surface provided with an elongated groove. The configuration of respective grooves is such that when the jaws are brought together to the position shown in FIG. 5, the grooves will encircle the outer surface of the separation column 27.

FIG. 5 also illustrates the aforementioned second suspension device for suspension of the second moveable wall-section 15. This second suspension device includes two piston-cylinder devices 52 which function to support the moveable second wall 15 at two mutually opposing side-parts thereof. In the case of the illustrated embodiment, the piston-cylinder device 52 is attached to the first wall-section 14 whereas the piston rod 53 of said device is attached to the second moveable wall 15. This arrangement enables the moveable wall 15 to move in the directions indicated by the arrow 18 in FIG. 1, between the position shown in FIG. 5, in which the card 21 is supported by the card holders 16 and 17, to the position shown in FIG. 6, in which the moveable wall 15 has been displaced to a position in which the card 21 rests solely along one long side thereof on the card holder 16 and will therefore fall gravitationally down into the waste chamber 1, between the two piston-cylinder devices 52.

Movement of the walls 14, 15, movement of the stepping motors, monitoring of the positions of the injector stems, depression of the injectors into the respective sleeves, and activation of the pinch valves are all controlled with the aid of known control electronics mounted in the electronics module 3. All of the process stages can be program-controlled, thereby enabling the method to be carried out fully automatically, from the moment of manually placing a card in the loading device 5.

The aforedescribed preferred and exemplifying embodiment of the invention can be modified and changed in many ways within the scope of the following claims.

For example, several cards can be placed sequentially in line between the first and the second card holders. Instead of only one loading device 5, two or more loading devices may be provided in the chemical chamber 2. Instead of using rodless piston-cylinder devices for the first and the second suspension devices 9, 52, there can be used a system of rails and rollers, of which latter one or more of the rollers may be driven. The pressure cylinder 47 may be replaced with a spring, a magnet or the like.

I claim:

1. A disposable kit for the preparation of radiopharmaceuticals with a radiotracer as a starting substance, comprising a card in a form of an elongated, rigid strip which is provided with a row of openings comprising one or more first openings and one or more second openings, means mounted around each of said one or more first openings and projecting out from one main surface of the rigid strip in a form of a sleeve for supporting a liquid injector on an inner surface of an inlet end of the sleeve and for connecting a hose at an outlet end of the sleeve, said supporting and connecting means being provided at the first openings but not being provided at the second openings, and a hydrolysis vessel, one opening of said one or more second openings adapted to support said hydrolysis vessel.

2. A disposable kit according to claim 1, further including a storage chamber, another opening of said second openings adapted to support the storage chamber, the storage chamber having a luer connection.

3. A disposable kit according to claim 1, further including a de-ionizing column, another opening of said second openings adapted to support the de-ionizing column, the de-ionizing column having connected thereto a discharge hose.

* * * * *